United States Patent [19]

Margules

[11] Patent Number: 4,791,932

[45] Date of Patent: Dec. 20, 1988

[54] EXTRACORPOREAL SENSING MODULE

[75] Inventor: Gary S. Margules, Miami, Fla.

[73] Assignee: Cordis Corporation, Miami, Fla.

[21] Appl. No.: 836,241

[22] Filed: Mar. 5, 1986

[51] Int. Cl.⁴ .............................................. A61B 5/00
[52] U.S. Cl. .................................... 128/632; 128/633; 128/635; 204/409
[58] Field of Search .............................. 128/632–633, 128/637, 639, 642, 635, 644; 204/409, 416, 418–420

[56] References Cited

U.S. PATENT DOCUMENTS

| | | | |
|---|---|---|---|
| 3,498,289 | 3/1970 | Watanabe et al. | 128/635 |
| 3,607,700 | 9/1971 | Tosteson . | |
| 3,657,095 | 4/1972 | Tosteson . | |
| 3,767,553 | 10/1973 | Brown, Jr. et al. . | |
| 3,957,037 | 5/1976 | Fletcher et al. | 128/644 |
| 4,053,381 | 10/1977 | Hamblen et al. . | |
| 4,197,852 | 4/1980 | Schindler et al. . | |
| 4,233,136 | 11/1980 | Spaziani et al. | 204/409 |
| 4,338,174 | 7/1982 | Tamura | 128/635 X |
| 4,340,457 | 7/1982 | Kater . | |
| 4,341,221 | 7/1982 | Testerman | 128/642 |
| 4,366,038 | 12/1982 | Kearney et al. . | |
| 4,437,970 | 3/1984 | Kitajima et al. . | |
| 4,444,498 | 4/1984 | Heinemann | 128/633 X |
| 4,459,199 | 7/1984 | Fletcher . | |
| 4,484,135 | 11/1984 | Ishihara et al. | 128/632 X |
| 4,487,679 | 12/1984 | Stare . | |
| 4,512,349 | 4/1985 | Hunt et al. | 128/632 |
| 4,516,580 | 5/1985 | Polanyi | 128/632 |
| 4,589,418 | 5/1986 | Gopikanth | 128/635 |
| 4,600,495 | 7/1986 | Fogt | 128/635 X |

*Primary Examiner*—Edward M. Coven
*Assistant Examiner*—Angela D. Sykes
*Attorney, Agent, or Firm*—Lockwood, Alex, Fitzgibbon & Cummings

[57] ABSTRACT

An extracorporeal sensing module for use in monitoring parameters of body fluids such as temperatures, concentrations of various ions, gases and other components, is in the form of a tube-like housing to receive the flow of body fluids such as blood therethrough and includes one or more spaced sensor assemblies which at least partially define the fluid flow lumen of the module in a manner as to establish isodiametric continuity for laminar flow of body fluids therethrough. Each sensor assembly of the module includes a convex portion, the innermost surface of which partially defines the lumen and is contiguous therewith to establish and maintain the isodiametric fluid flow path.

11 Claims, 1 Drawing Sheet

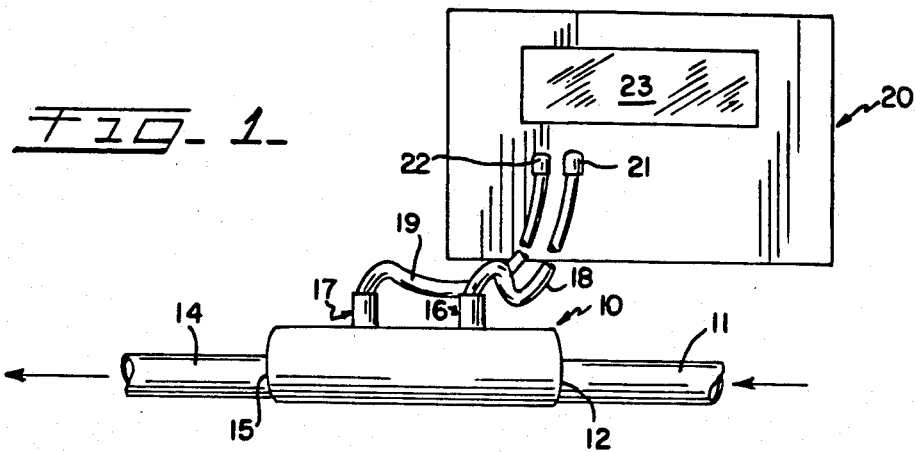
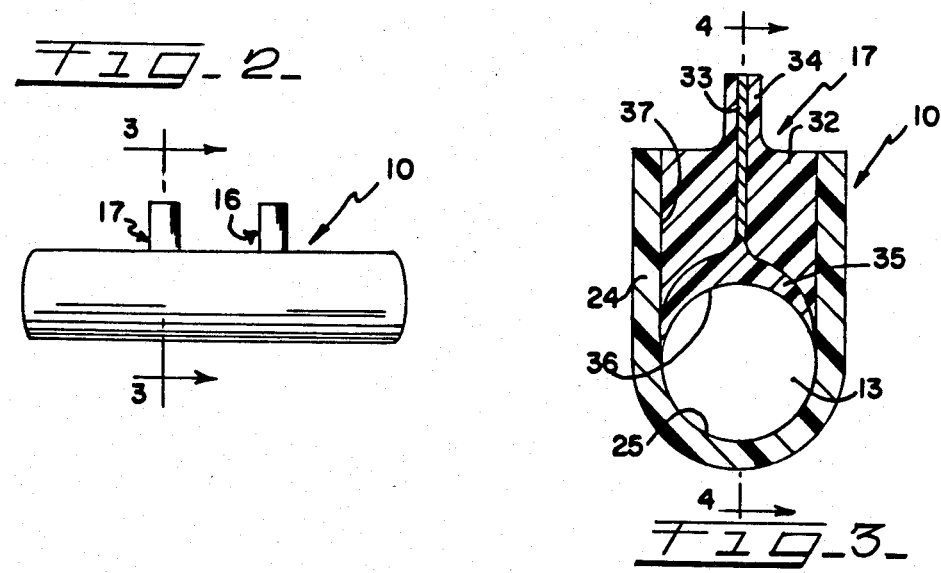
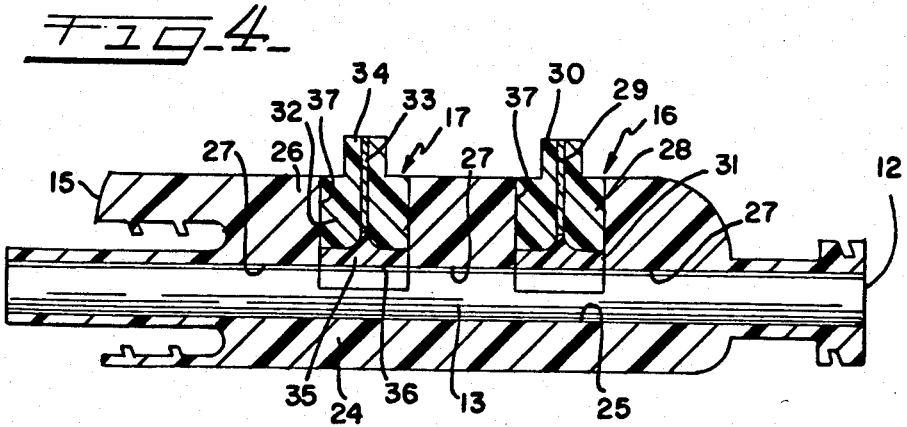

EXTRACORPOREAL SENSING MODULE

BACKGROUND AND DESCRIPTION OF THE INVENTION

The present invention generally relates to extracorporeal sensing modules for use in monitoring parameters of body fluids, and more particularly to an extracorporeal sensing module that has an internal surface that is a smooth and isodiametric cylinder throughout its length, which smooth internal surface continuously incorporates the surface of each electrode of the extracorporeal sensing module.

In instances of critical illness as well as critical surgical procedures such as open heart surgery, it is often mandatory to continuously monitor certain parameters of body fluids such as blood, this monitoring being with regard to temperatures, concentrations of various ions, concentrations of gases as well as concentrations of other components. In other less critical instances, such as dialysis, such monitoring is desirable. One approach for determining these types of parameters is to simply withdraw samples of the body fluid such as blood from the patient and to analyze same in vitro for ion and gas concentrations, for example. The results of such analytical procedures provide discrete information, and unless samples are taken with sufficient frequency, the results of such in vitro analyses might fail to timely indicate a trend. From a practical standpoint, there are limitations on the frequency of such in vitro sampling as generally dictated by the patient's status. Still further, the physician needs accurate and timely data, preferably continuous data, with regard to the development of any adverse or detrimental trends.

In vivo monitoring devices have been suggested and are available to monitor various parameters on a continuous basis. These devices include transcutaneous blood gas monitors such as those for measurement of oxygen or carbon dioxide tensions. Other devices have been designed to provide for direct measurement of ions, gases and other components of body fluids, such devices including an extracorporeal sensor module having a sensor protruding into the flow path of blood traversing a length of tubing. Devices of this type are often used, for example, to measure the concentration of potassium ions electrochemically, the potassium ion sensors being based on coated wire techniques with ion concentration being determined by potentiometric analysis.

Measurement of potassium, sodium, calcium and chloride ion concentrations are important in connection with many treatments and monitoring situations. For example, the potassium gradient is the principal contributor to normal functioning of all nervous and muscular tissue, especially the tissue of the heart. In the treatment of burns, diabetes, postcardiopulmonary by-pass, acute myocardial infarction as well as other intensive care conditions, the continuous measurement of potassium ion concentration is extremely important. Because of this importance, the description of the present invention will be directed primarily to the monitoring of potassium ion concentration while it will be understood that the sensing module of the present invention may also be used for monitoring of body fluids for other purposes, including but not limited to monitoring the concentration of other ions, gases or components.

Devices designed to date for in vivo monitoring have exhibited a common failing. Inadequate recognition of the importance of maintaining laminar flow of blood, for example, through the sensing module has prevailed. Projection of the sensor into the path of blood flow results in turbulence. The turbulent flow of blood increases the likelihood of entrapment of air bubbles, increases the likelihood of protein denaturation and can cause cell damage, each with its attendant problems. Cell damage can cause the cell contents to be released into the blood resulting in a higher concentration of the component, for example potassium ions, being measured than would exist in the blood without cell leakage. This detrimental result can be of major significance during surgery and treatment of critical conditions of the type referred to hereinabove. Additionally, turbulent flow of blood can result in clot formation.

Accordingly, there is a need for an improved extracorporeal sensing module for monitoring the parameters of body fluids. A general object of the subject invention is to provide such a module which is capable of establishing and maintaining laminar flow of body fluids therethrough while effectively analyzing or monitoring such body fluids.

Another object of this invention is to provide an extracorporeal flow cell or module which is of uncomplicated design and manufacture and in which the surface of the wall of the fluid flow passage is mutually defined by the module housing and by the sensing and reference electrode assemblies, thereby preventing the creation of turbulence by avoiding any projection of the sensor electrode assembly and/or reference electrode assembly into the path of fluid flow.

Still another object of the present invention is to provide an improved extracorporeal sensing module which provides an isodiametric fluid flow using sensor and/or reference electrode assemblies with confluent areas.

SUMMARY OF THE INVENTION

The present invention is directed to an extracorporeal sensing module for use in monitoring parameters of body fluids, which module includes a tube-like housing having inlet and outlet end portions for attachment with body fluid supply and discharge means. The fluid flow passageway or lumen that is internal of the housing and intended to be placed in communication with the body fluid supply and discharge means is cylindrical and is partially formed by one or more longitudinally spaced reference and sensing assemblies which also project out of the housing for connection with an external analyzer of known design. The reference and sensing assemblies each include convex portions, the innermost surfaces of which partially define the fluid flow lumen and are contiguous therewith to establish and maintain an isodiametric fluid flow path throughout the extracorporeal sensing module.

BRIEF DESCRIPTION OF THE DRAWINGS

The features of the present invention which are believed to be novel are set forth with particularity in the appended claims. The invention, together with the further objects and advantages thereof, may best be understood by reference to the following description, taken in conjunction with the accompanying drawings, in the several figures of which like reference numerals identify like elements, and in which:

FIG. 1 illustrates the extracorporeal sensing module of the present invention in elevation and connected for use in a body fluid analytical system, portions of the system being illustrated schematically and other portions being fragmented;

FIG. 2 is an elevational view of the module of the invention;

FIG. 3 is an enlarged cross-sectional view of the module of FIG. 2 as viewed along the line 3—3 thereof; and FIG. 4 is a longitudinal sectional view of the module taken along the line 4—4 of FIG. 3.

DESCRIPTION OF PREFERRED EMBODIMENT

FIG. 1 illustrates an extracorporeal blood oxygenation system including the blood flow sensing cell or module of the present invention, generally designated as 10. Tubing 11 constituting the blood supply means, which is attached to the inlet end 12 of the module 10, supplies blood flow from an extracorporeal blood oxygenator (not shown) or the like. Blood flows through the interior passageway or lumen 13 of the module 10 and into a discharge tube 14 attached to the discharge end 15 of the module. The tubing 14 typically returns the blood to the patient undergoing treatment. Illustrated module 10 includes a reference electrode assembly 16 and a sensor electrode assembly 17 having portions projecting radially upwardly from the module 10. Attached to these portions are appropriate leads or cables 18 and 19 which extend to an analyzer 20 of known type. The cables 18 and 19 are suitably connected to appropriate terminals 21 and 22 of the analyzer 20 as is also well known. The analyzer 20 includes a read-out area 23 which supplies the physician with the essential information obtained by the sensing module 10.

As best illustrated in FIG. 4, the blood supply end 12 of the module 10 is conveniently shaped to form a threaded male Luer-Lock type of fitting to accept a female Luer-Lock type of fitting (not shown) of the tubing 11 supplying blood from the oxygenator. The discharge end 15 of module 10 along the inner surface thereof in alignment with the lumen 13 of the module is conveniently shaped in the form of a threaded female Luer-Lock type of fitting to receive a male luer fitting (not shown) of the discharge tube 14. The lumen 13 as well as the lumen of the supply and discharge tubes 11 and 14 are of the same smooth cylindrical shape and diameter throughout so as to establish and maintain laminar flow.

Referring in particular to FIGS. 3 and 4, in at least the areas of the reference and sensor electrode assemblies, the module 10 is formed from a generally U-shaped housing member 24 which opens upwardly as viewed in FIG. 3. The housing member 24 may be formed of a biocompatible polymer, such as a clear polycarbonate and the like. The inner surface of the base portion 25 of the U-shaped housing member 24 forms the bottom portion of the lumen 13 along its inner surface The module 10 is completed externally of the electrode assemblies by the provision of a top housing portion 26 received between the upstanding legs of the U-shaped housing member 24. The top housing portion 26 includes one or more compartments 37 for receiving therein the reference and/or sensor electrode assemblies 16, 17 which, as best illustrated in FIG. 4, are longitudinally spaced along the module 10 and are in communication with the fluid flow passage or lumen 13. The top portion 26 of the housing may be formed from a suitable biocompatible polymer, such as a polycarbonate or the like, similar to the material out of which the U-shaped housing member 24 is made. The top housing portion 26 along its bottom surface 27 has a concave configuration which defines a portion of the upper surface of the lumen 13 thus establishing, with suitable surfaces of the assemblies 16, 17, a cylindrical fluid flow passageway longitudinally of the module 10 which is substantially smooth and isodiametric throughout its length.

Insert molded into each compartment 37 of the top portion 26 of the module 10 is the reference or sensor electrode assembly 16, 17. Each electrode assembly 16, 17 is of the same basic construction, although compartments thereof, notably the membranes, are selected for the particular intended use of the electrode assembly. Referring first to the reference electrode assembly 16, the body portion 28 thereof is preferably formed in place within the compartment 37, and may be formed from an epoxy resin which encapsulates a vertically extending conductor wire or electrode 29. The body portion 28 is provided with an upwardly and outwardly projecting terminal boss 30 through which the reference electrode 29 projects and to which the cable 18 is connected as shown in FIG. 1. Electrode 29 extends downwardly within the body portion 28 and is embedded in a convex reference member 31 that is formed of a material suitable for a reference electrode, for example, polyvinylchloride or the like. The bottom or inner surface of the membrane 31 is convex and is contiguous with the adjacent surfaces of the housing portions of the module 10 so as to establish and maintain the isodiametric integrity of the lumen 13 in the area of the reference electrode assembly 16 and without interposing any protruding edges or recessed inserts that would disturb laminar flow of fluid through the lumen 13.

Longitudinally spaced from the illustrated reference electrode assembly 16 is the sensor electrode assembly 17. The construction of assembly 17 is basically the same as that described in connection with the reference electrode assembly 16 and is best shown in FIGS. 3 and 4. The sensor electrode assembly 17 includes a body portion 32 that is preferably formed in place within compartment 37 and formed of suitable epoxy resin appropriately insert molded in the upper housing portion 26 of the module 10. Extending through the body portion 32 is a sensor electrode 33 suitably held by the body portion 32 by encapsulation. The top surface of the body portion 32 is provided with a radially upwardly projecting terminal boss 34 through which the top portion of the electrode 33 projects and to which the cable 19 is connected as illustrated in the system of FIG. 1. Bottom portion of the electrode 33 projects downwardly into a convex sensor membrane 35 which is made of material needed to achieve the desired sensing. When potassium ions are to be sensed, the sensor membrane 35 will be suitably formed from polyvinylchloride with its associated plasticizer and valinomycin, which material is sensitive to potassium ions as is well known. The sensor membrane 35 in its convex configuration presents a bottom surface 36 (FIG. 3) which is contiguous with the adjacent surfaces of the housing portions and is confluent therewith to establish and maintain the isodiametric integrity of the lumen 13 in the area of the sensor electrode assembly 17.

The reference electrode assembly 16 and the sensor electrode assembly 17 function to provide a potentiometric analysis of (in the illustrated embodiment) potassium ion concentration through voltage difference measurements in a known manner. Valinomycin is an ionophore specific for potassium ions, and the voltage difference measured in the illustrated embodiment is proportional to the concentration of potassium ions within the fluid such as blood flowing through the lumen 13.

The advantages of the present invention reside in the provision of fixed and configured reference and/or sensor membranes 31, 35 of a permanent and non-fluid nature. Still further, the membranes 31, 35 are configured to establish and maintain the integrity of the cylindrical fluid flow passage defined by the lumen 13 thereby establishing and maintaining laminar flow of body fluids therethrough and avoiding the many disadvantages attendant to turbulent flow. The module 10 is of uncomplicated design and is readily manufactured without attendant high cost. Monitoring results are accurate and not misleading due to additional cell damage caused by turbulence. While the reference electrode 29 is illustrated as being placed adjacent the fluid supply end 12 of the module, the positions of the electrodes 29 and 33 may be reversed to place the reference electrode 29 adjacent the discharge end 15 of the module. The internal isodiametric configuration of the lumen 13 provides greater overall biocompatibility in connection with the analysis of various body fluids for multiple purposes. The module of the present invention does not exhibit any detrimental effect to any body fluid being tested.

While a particular embodiment of the invention has been shown and described, it will be apparent to those skilled in the art that changes and modifications may be made without departing from the invention in its broader aspects, and, therefore, the aim in the appended claims is to cover all such changes and modifications as fall within the true spirit and scope of the invention.

I claim:

1. An extracorporeal sensing module for use in monitoring parameters of body fluids, comprising:
   a tube-like housing provided with inlet and outlet end portions for respective attachment with body fluid supply and discharge means;
   a lumen internally of said housing and extending longitudinally thereof for defining a fluid flow path in communication with said body fluid supply and discharge means, said lumen having an internal surface that is generally cylindrical and of substantially the same diameter throughout its longitudinal extent so that said lumen internal surface defines a substantially isodiametric fluid flow path; and
   a convex sensor membrane longitudinally spaced along and forming a part of said housing, said convex sensor membrane being constructed of polymeric material that is longitudinally spaced along said generally cylindrical internal surface, said polymeric material convex sensor membrane having a bottom surface which forms an inside surface thereof that is a flush portion of said generally cylindrical and substantially isodiametric lumen internal surface that defines the substantially isodiametric fluid flow path such that said fluid flow path defined by said substantially isodiametric lumen internal surface is unobstructed throughout its longitudinal extent, said flush portion bottom surface being contiguous with adjacent surfaces of said lumen internal surface, said convex sensor membrane having tapering ends, said contiguous flush portion bottom surface of the convex sensor membrane being reduced in cross-section toward and being confluent with said adjacent surfaces of the lumen.

2. The sensing module according to claim 1, wherein the diameter of said lumen is the same as the respective fluid flow diameters of said supply and discharge means.

3. The sensing module according to claim 1, wherein said housing includes a U-shaped member with the inner bottom surface thereof defining a bottom portion of said lumen, said sensor membrane being positioned in a top portion of said U-shaped member and defining a remaining top portion of said lumen.

4. The sensing module according to claim 3, wherein said sensor membrane includes a conductor which extends upwardly therefrom and projects outwardly of said housing.

5. The sensing module according to claim 4, wherein the diameter of said lumen is the same as the respective fluid flow diameters of said supply and discharge means.

6. The sensing module according to claim 3, wherein the diameter of said lumen is the same as the respective fluid flow diameters of said supply and discharge means.

7. The sensing module according to claim 1, wherein said sensor membrane is a sensing electrode assembly.

8. The sensing module according to claim 1, wherein said sensor membrane is a reference electrode assembly.

9. The sensing module according to claim 1, wherein said sensor membrane includes a sensing electrode assembly and a reference electrode assembly longitudinally spaced from each other along said substantially isodiametric lumen.

10. The sensing module according to claim 1, wherein said membrane includes an optical sensing assembly and a reference electrode assembly longitudinally spaced from each other along said substantially isodiametric lumen.

11. The sensing module according to claim 1, wherein said sensor membrane includes an electrochemical sensing assembly and a reference electrode assembly longitudinally spaced from each other along said substantially isodiametric lumen.

* * * * *